US012496190B2

(12) United States Patent
Rupp et al.

(10) Patent No.: US 12,496,190 B2
(45) Date of Patent: Dec. 16, 2025

(54) DELIVERY SYSTEM FOR PROSTHETIC HEART VALVE

(71) Applicant: EDWARDS LIFESCIENCES CORPORATION, Irvine, CA (US)

(72) Inventors: Kevin D. Rupp, Irvine, CA (US); Tung T. Le, Costa Mesa, CA (US); Thanh Huy Le, Oceanside, CA (US); Brian C. Gray, Trabuco Canyon, CA (US); Alejandro J. Froimovich Rosenberg, Sherman Oaks, CA (US); Jeff Lindstrom, Coto de Caza, CA (US); Kim D. Nguyen, Irvine, CA (US); Sonny Tran, Westminster, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 18/206,013

(22) Filed: Jun. 5, 2023

(65) Prior Publication Data

US 2023/0301783 A1 Sep. 28, 2023

Related U.S. Application Data

(63) Continuation of application No. 16/820,499, filed on Mar. 16, 2020, now Pat. No. 11,707,357, which is a
(Continued)

(51) Int. Cl.
*A61F 2/24* (2006.01)
*A61F 2/95* (2013.01)
(Continued)

(52) U.S. Cl.
CPC .......... *A61F 2/2433* (2013.01); *A61F 2/2418* (2013.01); *A61F 2/2436* (2013.01);
(Continued)

(58) Field of Classification Search
CPC ........ A61F 2/2418; A61F 2/2427–2436; A61F 2/95; A61F 2/958; A61F 2/962;
(Continued)

(56) References Cited

U.S. PATENT DOCUMENTS 5,417,707 A * 5/1995 Parkola ................ A61M 25/10 604/103.05
5,843,027 A * 12/1998 Stone ................... A61M 25/10 604/509
(Continued)

*Primary Examiner* — Sarah W Aleman
(74) *Attorney, Agent, or Firm* — Klarquist Sparkman, LLP; Joel B. German

(57) ABSTRACT

A delivery apparatus for implanting a radially compressible and expandable prosthetic heart valve in a native heart valve of the heart includes a handle portion and a balloon catheter assembly comprising an elongated balloon catheter shaft extending from the handle portion. The balloon catheter shaft includes a proximal end portion coupled to the handle portion and a distal end portion. The balloon catheter assembly further includes a balloon coupled to the distal end portion and configured to mount a prosthetic heart valve in a radially compressed state. A protective cover encapsulates the balloon, the cover defining a cavity shaped to accommodate the balloon.

18 Claims, 10 Drawing Sheets

Related U.S. Application Data continuation of application No. 15/252,110, filed on Aug. 30, 2016, now Pat. No. 10,588,744.

(60) Provisional application No. 62/214,424, filed on Sep. 4, 2015.

(51) Int. Cl.
*A61M 25/01* (2006.01)
*A61M 25/10* (2013.01)

(52) U.S. Cl.
CPC ........ *A61F 2/9517* (2020.05); *A61M 25/0136* (2013.01); *A61M 2025/1081* (2013.01)

(58) Field of Classification Search
CPC ............... A61F 2/966; A61M 25/0113; A61M 25/0136; A61M 25/10; A61M 25/1006; A61M 2025/1081; B65D 77/00
See application file for complete search history.

(56) References Cited

U.S. PATENT DOCUMENTS 6,152,944 A * 11/2000 Holman .................. A61F 2/958 606/198
7,105,013 B2 * 9/2006 Durcan ................. A61M 25/10 623/1.11
10,702,673 B2 * 7/2020 Traxler ................. A61M 25/10
11,000,679 B2 * 5/2021 Kokate ............ A61M 25/1038
2004/0093005 A1 * 5/2004 Durcan ................. A61M 25/10 606/194
2004/0267195 A1 * 12/2004 Currlin ............ A61M 25/1006 604/103.1
2008/0086192 A1 * 4/2008 WasDyke ............. A61F 2/0095 623/1.12
2011/0015729 A1 * 1/2011 Jimenez ........... A61M 25/0136 623/2.11
2011/0184509 A1 * 7/2011 Von Oepen ............... A61F 2/95 623/1.23
2015/0088240 A1 * 3/2015 Lam ........................ A61F 2/958 156/196
2016/0249969 A1 * 9/2016 Santoinanni ........... A61B 18/02 606/24

* cited by examiner

DELIVERY SYSTEM FOR PROSTHETIC HEART VALVE

CROSS REFERENCE TO RELATED APPLICATIONS

This application is a continuation of U.S. application Ser. No. 16/820,499, filed Mar. 16, 2020, which is a continuation of U.S. application Ser. No. 15/252,110, filed Aug. 30, 2016, which claims the benefit of U.S. Provisional Application No. 62/214,424, filed Sep. 4, 2015. Each of the above applications is incorporated herein by reference in its entirety.

FIELD

The present disclosure concerns embodiments of delivery systems for implanting prosthetic heart valves.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise or death. For many years the definitive treatment for such disorders was the surgical repair or replacement of the valve during open heart surgery, but such surgeries are prone to many complications. More recently, a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve such as by inflating a balloon on which the prosthetic valve is mounted. Alternatively, the prosthetic valve can have a resilient, self-expanding stent or frame that expands the prosthetic valve to its functional size when it is advanced from a delivery sheath at the distal end of the catheter.

A prosthetic valve that has a relatively large profile or diameter in the compressed state can inhibit the physician's ability to advance the prosthetic valve through the femoral artery or vein. More particularly, a smaller profile allows for treatment of a wider population of patients, with enhanced safety. Thus, a need exists for delivery devices that can minimize the overall crimp profile of the prosthetic valve for the delivery of the prosthetic valve through the patient's vasculature.

Relatively long delivery devices, such as used for transfemoral delivery of a prosthetic valve, can inhibit the physician's ability to position the prosthetic valve precisely at the desired implantation site because the forces applied to the handle at one end of the delivery device can cause unwanted movement of the prosthetic valve at the opposite end of the delivery device. Thus, a need exists for delivery devices that allow a physician to accurately control the positioning of the prosthetic valve at the desired implantation location.

Known delivery devices typically require a physician to use both hands when positioning the prosthetic valve at the implantation site. Additionally, in certain circumstances, control mechanisms for positioning the prosthetic valve can become jammed or kinked during operation. Thus, a need exists for delivery devices with improved control mechanisms for positioning valves.

SUMMARY

Certain embodiments of the disclosure relate to devices and methods for implanting prosthetic heart valves. In one representative embodiment, a delivery apparatus for implanting a radially compressible and expandable prosthetic heart valve in a native heart valve of the heart comprises a handle portion and an elongated shaft extending from and movable relative to the handle portion. The shaft comprises a proximal end portion coupled to the handle portion and a distal end portion configured to mount a prosthetic heart valve in a radially compressed state. The handle portion comprises a control member movable longitudinally with respect to the handle portion, the control member engaging a gear assembly operable to convert longitudinal motion of the control member to rotational motion of the gear assembly. The gear assembly engages the elongated shaft such that rotational motion of the gear assembly causes corresponding longitudinal motion of the elongated shaft relative to the handle portion.

In another representative embodiment, a method of implanting a radially compressible and expandable prosthetic heart valve in a native valve of the heart comprises introducing a delivery device into the body of a patient, the delivery device comprising a handle portion, an elongated shaft extending from the handle portion, the shaft having a distal end portion mounting a prosthetic heart valve in a radially compressed state. The method further comprises advancing the distal end portion of the delivery device toward the native heart valve until the prosthetic valve is within or adjacent the aortic arch, wherein the act of advancing comprises pushing the handle portion distally so as to push the delivery device distally through the patient toward the native heart valve. The method further comprises steering the delivery device through the aortic arch by rotating a rotatable member coupled to the handle portion, rotation of the rotatable member causing corresponding flexing or unflexing of the elongated shaft. The method further comprises axially positioning the prosthetic heart valve at a desired implantation position by moving a lever member coupled to the handle portion, wherein proximal and distal motion of the lever member causes corresponding proximal and distal motion of the elongated shaft relative to the handle portion. The method further comprises radially expanding the prosthetic heart valve to engage the annulus of the native heart valve after the prosthetic heart valve has been moved to the desired implantation position.

In another representative embodiment, a delivery apparatus for implanting a radially compressible and expandable prosthetic heart valve in a native heart valve of the heart comprises a handle portion, and an elongated balloon catheter shaft extending from the handle portion. The balloon catheter shaft includes a proximal end portion coupled to the handle portion and a distal end portion, and further comprises a balloon mounted on the distal end portion and configured to mount a prosthetic heart valve in a radially compressed state. The delivery apparatus further includes a steerable guide shaft disposed coaxially about the balloon catheter shaft and including a proximal end portion coupled to the handle portion and a distal end portion. The delivery apparatus further includes a positioning assembly including a lever member coupled to the proximal end portion of the balloon catheter shaft such that longitudinal motion of the lever member causes corresponding longitudinal motion of the balloon catheter shaft with respect to the guide shaft and the handle portion. The delivery apparatus further comprises a steering assembly including a rotatable member and a pull wire having a proximal end portion operatively connected to the rotatable member and a distal end portion fixed to the distal end portion of the guide shaft such that rotation of the rotatable member causes corresponding flexing and unflexing of the respective distal end portions of the guide shaft and the balloon catheter shaft. The rotatable member of the steering assembly and the lever member of the positioning assembly are substantially co-located along a longitudinal axis of the balloon catheter shaft such that the rotatable member and the lever member are operable with one hand.

The foregoing and other objects, features, and advantages of the disclosure will become more apparent from the following detailed description, which proceeds with reference to the accompanying figures.

DETAILED DESCRIPTION

In particular embodiments, a delivery apparatus for implanting a prosthetic, transcatheter heart valve via a patient's vasculature includes one or more adjustment devices for adjusting the position of a balloon member including a prosthetic valve radially crimped thereon. The balloon member can be mounted on a distal end of a balloon catheter extending coaxially within a guide (or flex) catheter. As described below in more detail, the balloon member and the crimped prosthetic valve can enter the vasculature of a patient through an introducer sheath and, once the balloon member and the crimped prosthetic valve reach a suitable location in the body, the prosthetic valve can be expanded at the treatment site (e.g., the native aortic valve). The one or more adjustment devices can further be used to accurately adjust or "fine tune" the position of the prosthetic valve relative to the desired deployment location.

Figure 1:
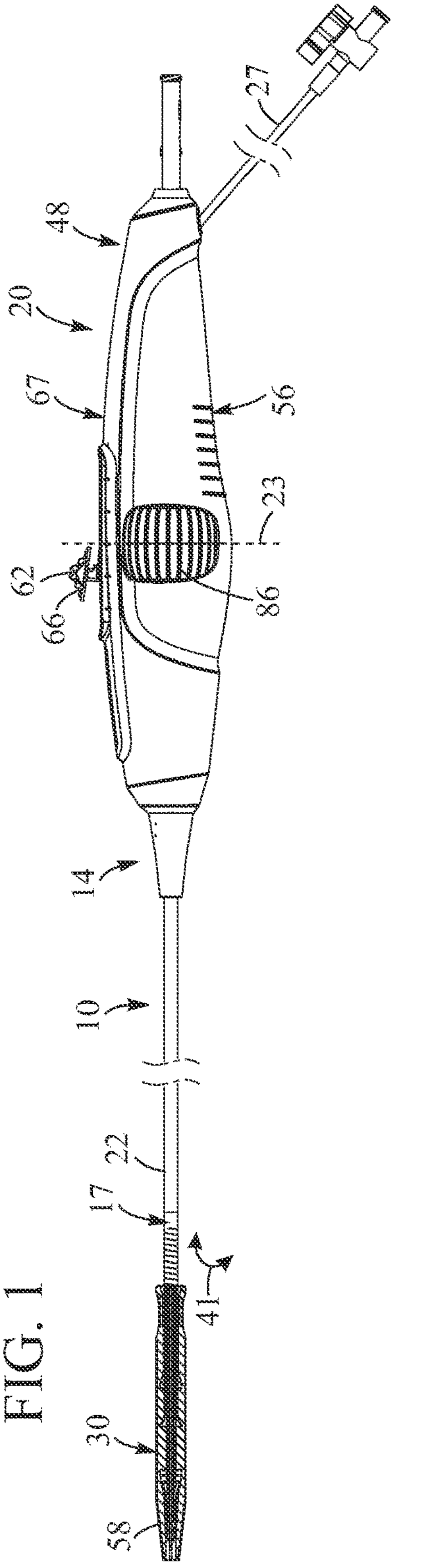
FIG. 1 illustrates a representative embodiment of a delivery apparatus for implanting a prosthetic heart valve, according to one embodiment.

FIG. 1 shows a delivery apparatus 10 adapted to deliver a prosthetic heart valve 12 (e.g., a prosthetic aortic valve) to a heart, according to one embodiment. The apparatus 10 generally includes a first elongated shaft configured as a steerable guide catheter 14, and a second elongated shaft configured as a balloon catheter 16 extending through the guide catheter 14. The guide catheter can also be referred to as a flex catheter or a main catheter. The use of the term main catheter should be understood, however, to include flex or guide catheters, as well as other catheters that do not have the ability to flex or guide through a patient's vasculature.

The guide catheter 14 and the balloon catheter 16 in the illustrated embodiment are adapted to slide longitudinally relative to each other to facilitate delivery and positioning of the prosthetic valve 12 at an implantation site in a patient's body, as described in detail below.

Figure 2:
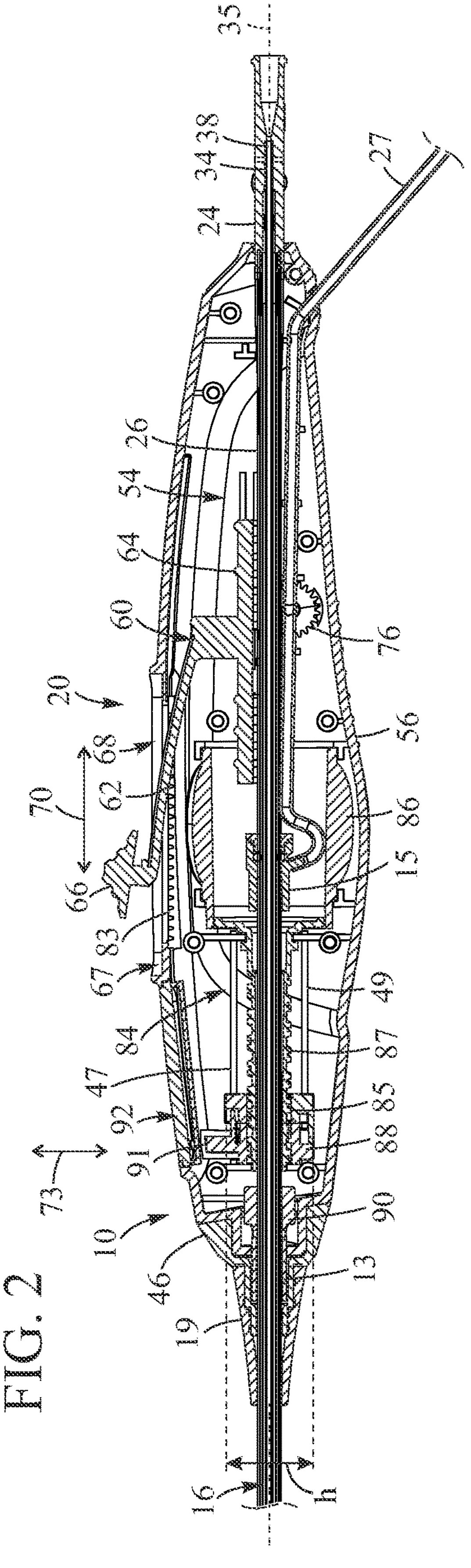
FIG. 2 is a cross-sectional view of a handle portion of the delivery apparatus of FIG. 1.

The guide catheter 14 includes a handle portion 20 and an elongated guide tube, or shaft, 22 extending from handle portion 20. FIG. 2 shows the guide catheter shaft 22 extending from the handle portion 20 over the balloon catheter 16. The guide catheter 14 can also include a steerable portion generally indicated at 17 (FIG. 1), the curvature of which can be adjusted by the operator to assist in guiding the apparatus through the patient's vasculature and, in particular, the aortic arch, as further described below. The steerable portion 17 can be coupled to a control device of the handle portion by at least one pull wire 18, such that tensioning and releasing the pull wire causes corresponding flexing and unflexing of the steerable section 17 of the guide catheter 14 and, hence, of the balloon catheter 16, as indicated by arrow 41 and further described below.

In the illustrated embodiment, the balloon catheter 16 includes a proximal port 24 (FIGS. 2 and 3) adjacent handle portion 20, and an elongated outer balloon catheter shaft 26 that extends from the proximal port 24 and through handle portion 20 and guide tube 22. The handle portion 20 can include a side arm 27 which can be, for example, a flush tube having an internal passage that fluidly communicates with a lumen defined by the handle portion 20. In the illustrated embodiment, the guide tube 22 can terminate at or adjacent a seal member 15 where the flush tube 27 connects with an inner passage defined by the balloon catheter 16 further described below.

Figure 4:
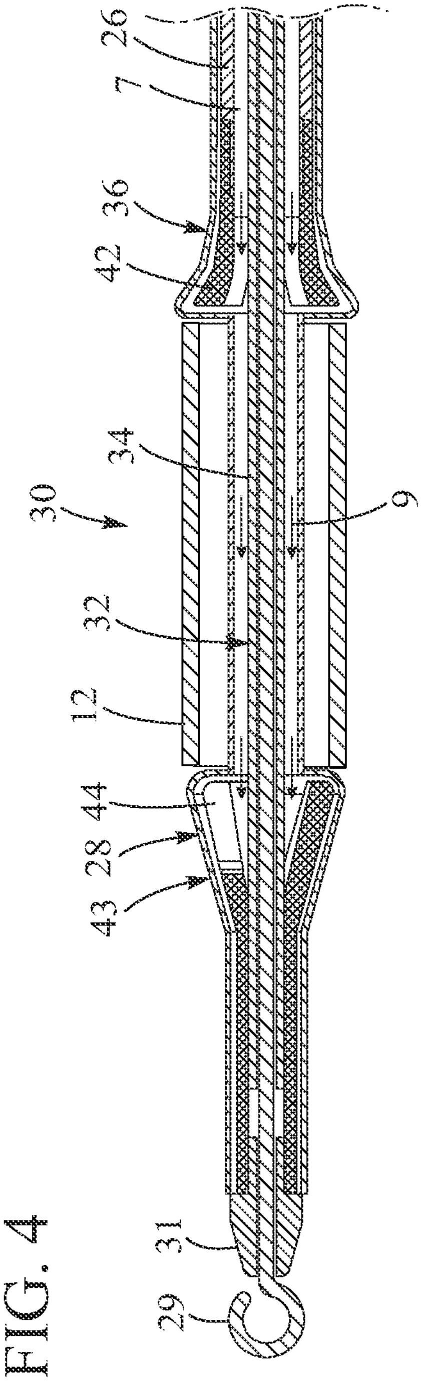
FIG. 4 is a cross-sectional view of a distal end portion of the delivery apparatus of FIG. 1.

An inflatable balloon 28 can be mounted at the distal end of the balloon catheter 16. As shown in FIG. 4, the delivery apparatus 10 is configured to mount the prosthetic valve 12 in a crimped state over the balloon 28 for insertion of the delivery apparatus and prosthetic valve into a patient's vasculature.

Figure 3:
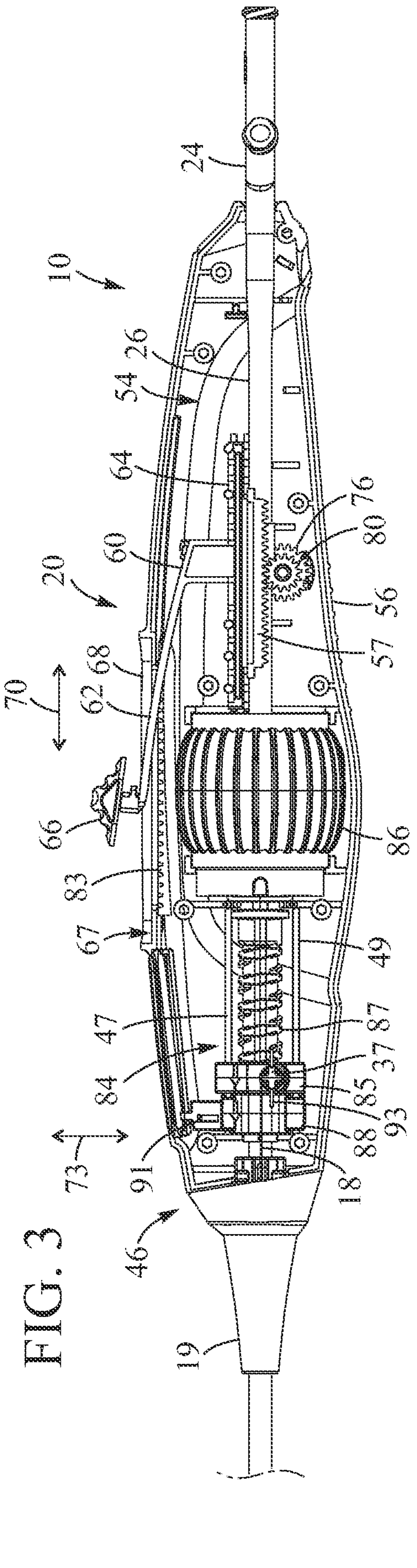
FIG. 3 is a side elevation view of the handle portion with a portion of the shell removed to illustrate the interior of the handle portion.

As shown in FIGS. 2, 3 and 4, the balloon catheter 16 in the illustrated configuration further includes an inner balloon catheter shaft 34 that extends from the proximal port 24 and coaxially through the outer balloon catheter shaft 26 and the balloon 28. The balloon 28 can be supported on a balloon mounting portion 30 disposed on a distal end portion 32 of the outer shaft 26. FIG. 4 illustrates the distal end portion of the delivery apparatus in greater detail. A proximal end portion 36 of the balloon can be folded around a proximal collar member 42 (also referred to as a "stop") of the balloon mounting portion 30 mounted on the end of the outer shaft 26 of the balloon catheter and a distal end portion 43 of the balloon 28 can be folded around a distal collar member 44 of the balloon mounting portion mounted on the distal end portion of the inner shaft 34 of the balloon catheter. In certain embodiments, the distal end of the guide catheter shaft 22 terminates proximal to the proximal end of the balloon 28. A proximal end portion of the balloon can be secured to the outer balloon catheter shaft 26 or the guide catheter shaft 22. A distal end portion of the balloon can be secured to a nose cone 31 disposed on or otherwise coupled to the inner shaft 34. In some embodiments, after the balloon 28 is folded around the balloon catheter shaft and the collar members 42, 44, the assembly can be covered by a protective cap or cover 58 (FIG. 1) for storage and/or shipment.

The outer diameter of the inner balloon catheter shaft 34 can be sized such that an annular space 7 is defined between the inner and outer balloon catheter shafts along the entire length of the outer balloon catheter shaft 26. The proximal port 24 of the balloon catheter 16 can be formed with a fluid passageway that is fluidly connectable to a fluid source (e.g., saline) to inflate the balloon and flush the space between the inner and outer balloon catheter shafts. Thus, the fluid passageway can be in fluid communication with the annular space 7 between the inner balloon catheter shaft 34 and the outer balloon catheter shaft 26 such that fluid from the fluid source can flow through the fluid passageway, through the space between the shafts, and into the balloon 28 to inflate the same and deploy the prosthetic valve 12. FIG. 4 illustrates the flow of fluid (indicated by arrows 9) through the annular space 7 and through passages in the proximal and distal shoulders 42 and 44. The fluid can then flow into the proximal and distal end portions 36, 43 of the balloon 28 to expand the valve 12.

The inner balloon catheter shaft 34 can also define a lumen 38 (FIG. 2) that is sized to receive a guide wire 29 that can extend coaxially through the inner balloon catheter shaft 34 and optionally through the nose cone 31, as shown in FIG. 4.

The inner balloon catheter shaft 34 and the outer balloon catheter shaft 26 of the balloon catheter can be formed from any of various suitable materials, such as nylon, braided stainless steel wires, or a polyether block amide (commercially available as Pebax), to name a few. The shafts 26, 34 can have longitudinal sections formed from different materials in order to vary the flexibility of the shafts along their lengths. The inner balloon catheter shaft 34 can have an inner liner or layer formed of Teflon® to minimize sliding friction with a guide wire. The shafts 26, 34 can also be coaxial about a longitudinal axis 35 (FIG. 2) of the balloon catheter 16, and can be axially movable relative to the handle portion 20 and guide catheter 14 along the axis 35.

The handle 20 in the illustrated embodiment can comprise first and second shell portions 50, 52 (FIG. 5) couplable to one another to define an interior cavity 54 (FIGS. 2 and 3). The handle 20 can also include a grip portion 56 engageable by, for example, a user's fingers such that the handle can be held with the thumb disposed adjacent a top portion 67 of the handle.

As best shown in FIGS. 2 and 3, the handle portion 20 can include an axial position control assembly 60 and a steering or angular position control assembly 84 for steering the delivery apparatus through the aortic arch and positioning the balloon and prosthetic valve in the annulus of a native heart valve. The axial position control assembly 60 can include an activator or control member configured as a lever member 62 coupled to a base member 64 disposed within the handle portion 20 adjacent the outer balloon catheter shaft 26. The lever member 62 can include a grip portion 66 engageable by a user (e.g., with the thumb), and can be axially movable along a slot 68 defined in the top portion 67 of the handle such that axial movement of the lever member causes corresponding axial movement of the base member within the handle portion in the directions indicated by arrow 70.

Figures 5, 6:
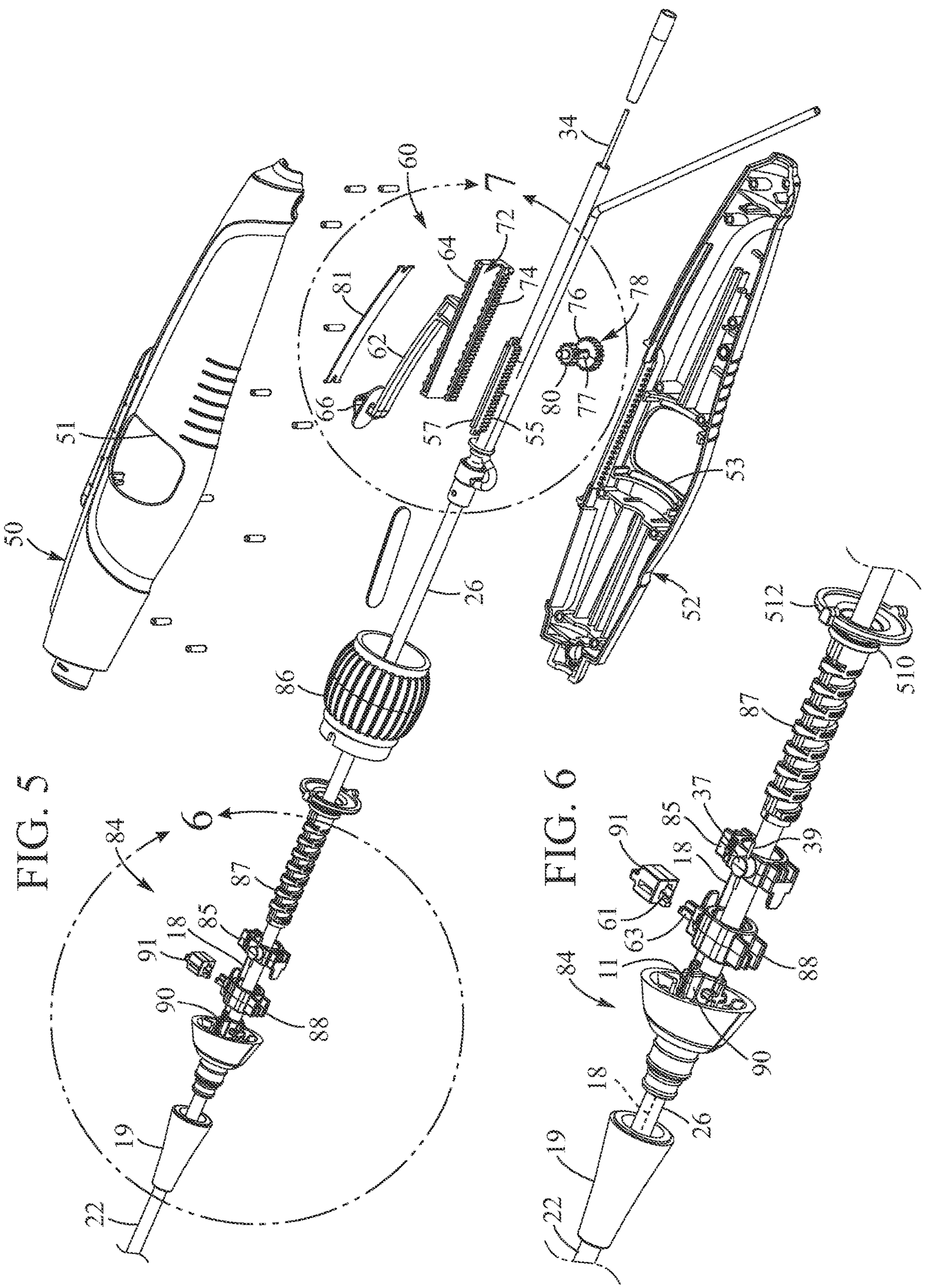
FIG. 5 is an exploded view of the handle portion of the delivery apparatus of FIG. 1.
FIG. 6 is an exploded view of a steering assembly of the delivery apparatus of FIG. 1.
Figure 7:
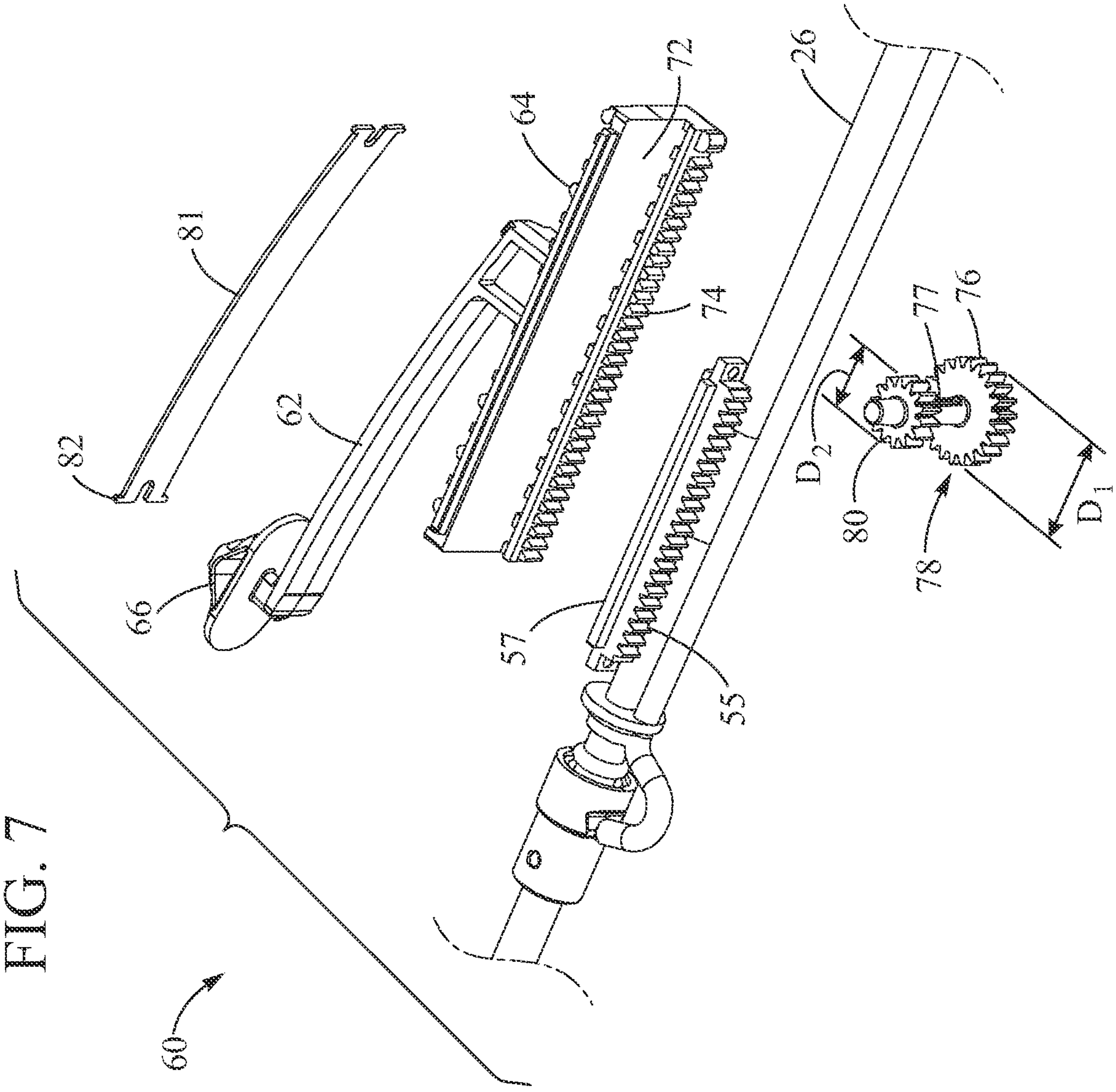
FIG. 7 is an exploded view of an axial position control assembly of the delivery apparatus of FIG. 1.

Referring to FIGS. 5 and 7, a lower surface 72 of the base member 64 can include a plurality of teeth or cogs 74 arranged longitudinally along a length of the base member on a side of the base member corresponding to the second shell portion 52 in the illustrated embodiment. The cogs 74 can engage with teeth of a first gear 76 mounted on a shaft 77 of a gear assembly 78 configured as a compound gear extending transverse to the balloon catheter shaft 26 such that axial motion of the base member 64 causes corresponding rotational motion of the gear assembly 78. In the illustrated embodiment, the shaft 77 of the gear assembly 78 can extend beneath the balloon catheter shaft 26, and the gear assembly can further include a second gear 80 disposed on the shaft 77 on the opposite side of the balloon catheter shaft 26 from the first gear 76. The teeth of the second gear 80 can engage cogs 55 of a rack member 57 coupled to the balloon catheter shaft 26. In this manner, longitudinal motion of the lever member 62 can be converted to rotational motion of the gear assembly 78 by interaction of the base member 64 with the first gear 76, and rotational motion of the second gear 80 can be converted to longitudinal motion of the balloon catheter shaft 26 in the same direction as the lever member by interaction of the second gear with the rack member 57. Thus, longitudinal motion of the lever member 62 can produce longitudinal motion of the balloon catheter shaft 26 (and, hence, of the prosthetic valve 12) in the proximal and distal directions relative to the handle 20 via rotational motion of the gear assembly 78.

As illustrated in FIG. 7, the first gear 76 can have a diameter $D_1$ and the second gear 80 can have a diameter $D_2$, and the first gear can be larger than the second gear such that the ratio $D_2/D_1$ defines a gear reduction ratio of the gear assembly 78. Thus, the gear assembly 78 can be operable such that longitudinal motion of the lever member 62 by a given distance results in longitudinal motion of the balloon catheter member 26 that is reduced by a factor corresponding to the gear reduction ratio. For example, in some embodiments, the gear reduction ratio can be from about 1.1:1 to about 5:1. In some embodiments, the gear reduction ratio can be from about 1.1:1 to about 3:1. In some embodiments, the gear reduction ratio can be about 2:1. In some embodiments, the gear reduction ratio can be about 1.3:1. In this manner, the axial position control assembly 60 can provide "fine" axial position control of the balloon catheter member 26 (and, hence, of the prosthetic valve 12) at the target implantation site after the valve has been advanced to the vicinity of the implantation site. Gear reduction ratios such as those given above can also provide mechanical advantage or force amplification of motion inputs to the lever member by a user, allowing the control assembly 60 to be operated with a single thumb or finger. Owing to the position of the first and second gears 76, 80 on opposite sides of the balloon catheter shaft 26, the gear assembly 78 can also be self-centering about the balloon catheter shaft 26 to promote smooth operation and reduce binding.

In the illustrated embodiment, the assembly 60 also includes a locking member 81 disposed adjacent the lever member 62 and configured as a leaf spring in the illustrated embodiment. In the illustrated embodiment, the locking member 81 is mounted on the lever member 62 and serves as a biasing member to bias the lever member away from the base member 64. The locking member 81 can include one or more protrusions 82 operable to engage teeth or cogs 83 (FIGS. 2 and 3) located along one or both sides of the slot 68. In this manner, when the lever member 62 is depressed by a user, the locking member 81 can be elastically deflected inwardly relative to the handle such that protrusions 82 disengage from the cogs 83, allowing motion of the lever member in the slot. When the lever member 62 is released, the locking member 81 can return to its non-deflected state and the protrusions 82 can engage the adjacent cogs 83 of the handle portion 20, preventing inadvertent motion of the lever member and, hence, of the balloon catheter shaft 26. In some embodiments, the handle can also include indicator markings or the like adjacent the slot 68 to indicate a position of the balloon catheter shaft 26 relative to the guide catheter 14.

Referring to FIGS. 5 and 6, the steering assembly 84 can include an activating member or control member configured as a rotatable member or knob 86 coupled to a threaded shaft 87. The threaded shaft 87 can be disposed coaxially about the balloon catheter shaft 26 such that rotation of the rotatable member 86 causes corresponding rotation of the threaded shaft about the balloon catheter shaft. The assembly 84 can further include a pull wire attachment member 85 and a tension member 88. The pull wire 18 can be coupled to the attachment member 85, and can extend distally through a pull wire lumen of the shaft 22 of the guide catheter 14. In the illustrated embodiment, a proximal end portion of the pull wire 18 can be fixedly secured to a post 37 of the attachment member 85, and a distal end portion of the pull wire 18 can be fixedly secured at a location along the steerable section 17. In some embodiments, the post 37 can include one or more tie-down members 39 about which the pull wire 18 can be wrapped or tied to secure the wire to the post.

The attachment member 85 and the tension member 88 can be movably disposed on the threaded shaft 87. For example, the attachment member 85 and the tension member 88 can include grooves corresponding to the threads of the threaded shaft 87 such that rotation of the threaded shaft 87 causes longitudinal motion of the attachment member and the tension member along the threaded shaft in the directions indicated by arrow 89 (FIGS. 2 and 3) between a proximal position and a distal position. In this manner, motion of the attachment member 85 along the threaded shaft 87 attendant to rotation of the rotatable member 86 can apply or relieve tension in the pull wire 18 cause flexing and unflexing of the steerable section 17. For example, moving the attachment member 85 to the proximal end of the threaded shaft 87 corresponds to a fully flexed position of the guide catheter relative to the longitudinal axis 35, and moving the attachment member to the distal end of the threaded shaft corresponds to an unflexed position of the guide catheter relative to the longitudinal axis 35.

The attachment member 85 and the tension member 88 can also travel along guide members 47, 49 extending parallel to the threaded shaft 87, as best shown in FIGS. 2 and 3. In the illustrated embodiment, the guide members 47, 49 are tabs extending from the first shell 50 of the handle portion, with the guide member 47 disposed above the threaded shaft 87 and the guide member 49 disposed below the threaded shaft. The guide members 47, 49 can be received in, for example, corresponding grooves or openings defined in the attachment member 85 and the tension member 88, respectively, and can reduce or prevent rotation of the attachment member and the tension member as they move along the threaded shaft 87. In alternative embodiments, the guide members 47, 49 can extend from either the first or second shells 50, 52 of the handle portion 20. In further alternative embodiments, the guide members 47, 49 can be configured as, for example, rods extending longitudinally parallel to the threaded shaft 87.

In the illustrated embodiment, the pull wire 18 can enter the handle portion 20 at a location adjacent a tapered section 19 of the guide catheter. As the pull wire 18 extends proximally from the tapered section 19 into the handle portion 20, the pull wire can be guided or lifted radially away from the outer diameter of the balloon catheter shaft 26 by a ramp member 90 to a diameter or height h of the tension member 88 and/or attachment member 85, and can extend across the tension member to the attachment member.

Figure 9:
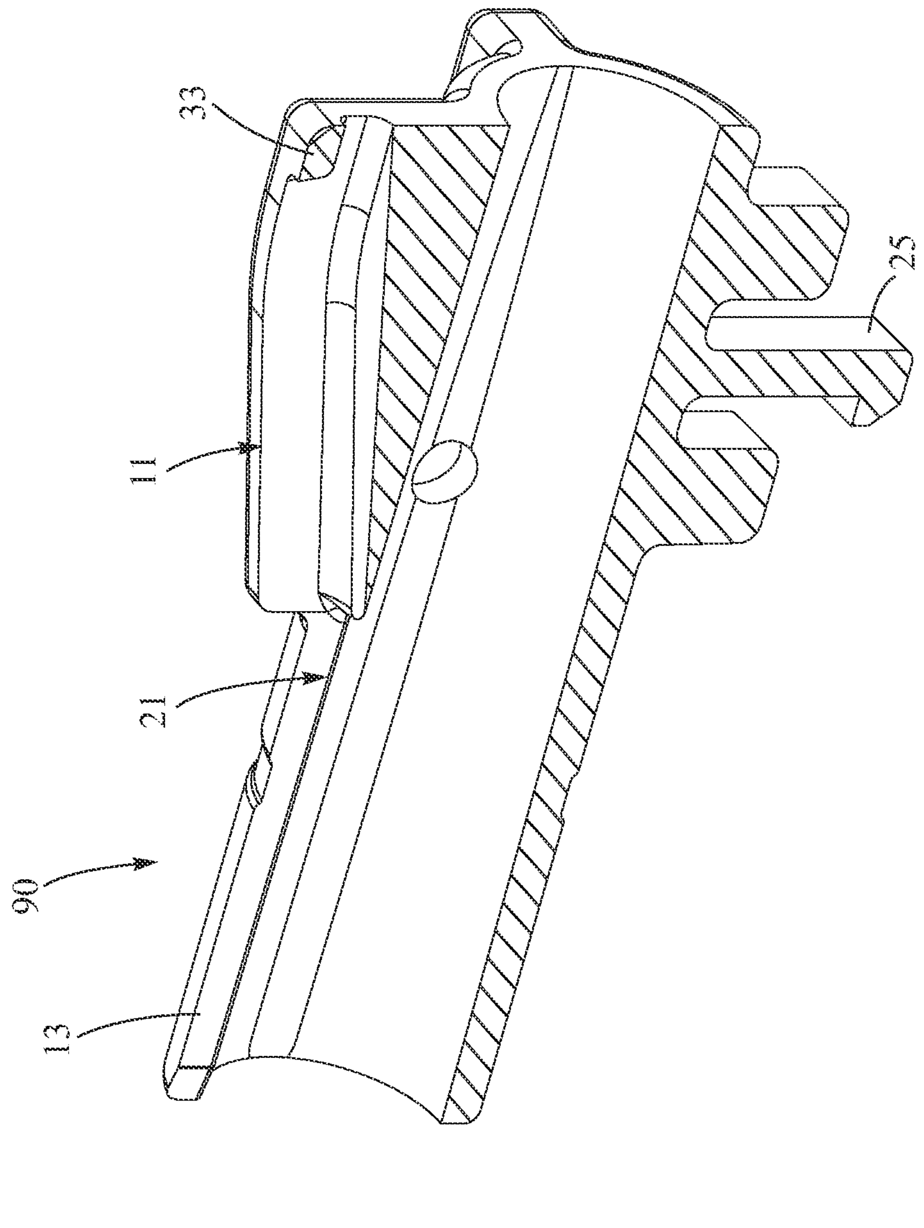
FIG. 9 is a cross-sectional side elevation view of a representative embodiment of a ramp member.

FIG. 9 illustrates the ramp member in greater detail. In the illustrated embodiment, the ramp member 90 can include a distally extending cylindrical portion 13 and an inclined ramp portion 33. The ramp portion 33 can define a channel 11 sized to receive the pull wire 18, and can guide the unconstrained portion of the pull wire exiting the lumen of the guide shaft 22 into the handle portion. In the illustrated embodiment, the pull wire 18 can exit the pull wire lumen of the guide shaft 22 distally of the ramp portion 33 and can extend between the guide shaft and the ramp member through a slot or other opening defined in the cylindrical portion 13. By gradually lifting the pull wire 18 away from the axis of the pull wire lumen, the channel 11 of the ramp member 90 can reduce the likelihood of the pull wire binding or buckling within the handle portion when, for example, the attachment member 85 moves distally along the threaded shaft 87 such that tension in the pull wire is relieved (e.g., attendant to unflexing the steerable section 17 of the guide catheter). The ramp member 90 can also include a latching pawl 25 to engage and couple the ramp member to the handle portion 20.

As illustrated in FIG. 9, the ramp member 90 can also define a lumen 21 extending the length of the member and configured to receive the guide shaft 22. A proximal portion of the lumen 21 can be tapered such that the walls of the lumen engage and retain the guide shaft 22, while a distal portion of the lumen has a diameter greater than the diameter of the guide shaft and does not contact the guide shaft when it is in a non-deflected state. In some embodiments, an adhesive can be applied at least to the tapered portion of the lumen 21 to aid in retaining the guide shaft 22. In this manner, the ramp member 90 can provide strain relief for the guide shaft 22 as it is flexed, helping to reduce or prevent buckling of the guide shaft within the handle portion 20 when the guide shaft is flexed.

The tension member 88 can be disposed on the threaded shaft 87 adjacent the attachment member 85 and, in some embodiments, coupled to the attachment member, such that the tension member and the attachment member move together along the threaded shaft. As the attachment member 85 moves proximally along the threaded shaft 87 by rotation of the rotatable member 86 (corresponding to flexing of the guide catheter), the tension member 88 can prevent the attachment member from moving distally along the threaded shaft when manual pressure is released from the rotatable member. For example, a user can rotate the rotatable member 86 until a selected degree of flexion of the guide catheter is achieved (e.g., corresponding to a desired angle of the prosthetic valve relative to the native heart valve at the implantation site). When the user releases the rotatable member 86, the tension member 88 can retain the attachment member 85 at the position on the threaded shaft 87 corresponding to the selected degree of flexion so that the guide catheter does not inadvertently unflex (owing to, for example, a thread pitch that provides sufficient friction to prevent movement of the tension member without force application by a user).

Thus, by keeping the attachment member 85 at the selected position on the threaded shaft 87, the tension member 88 maintains tension in the pull wire 18 when the guide catheter is flexed. The tension member 88, in combination with channel 11 of the ramp member 90, can also reduce or prevent kinking of the pull wire 18 inside the handle portion 20 when the guide catheter is unflexed by guiding the pull wire into the lumen of the guide catheter, and by allowing any extra length of the pull wire to remain in a slackened state within the handle portion. This can be especially advantageous when the guide catheter is unflexed in a curved or constrained anatomy (for example, the aortic arch), in which the guide catheter cannot fully straighten.

The steering assembly 84 can also include a visual indicator 91 coupled to, for example, the tension member 88, and configured to move proximally and distally therewith in a window or slot 92 defined in the distal portion 46 of the handle 20. In this manner, the indicator 91 can indicate a degree of flexion of the guide catheter to a user based upon the location of the tension member 88 within the handle portion 20. In the illustrated embodiment, the slot 92 can be inclined in a generally proximal direction according to the shape of the distal handle portion 20.

Figure 8:
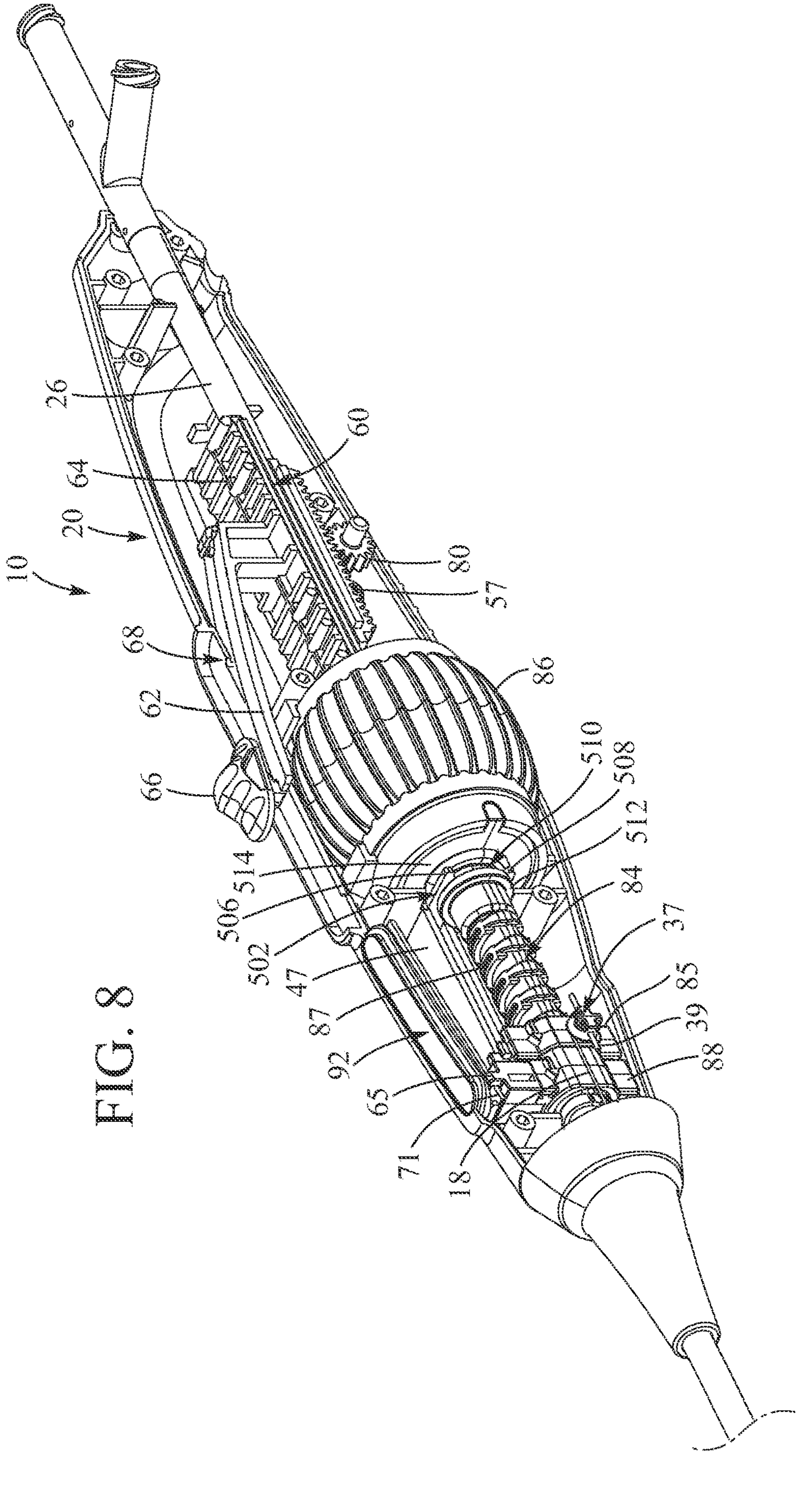
FIG. 8 is a perspective view of the handle portion with a portion of the shell removed to illustrate the interior of the handle portion.

As best shown in FIG. 6, the visual indicator 91 can define an opening 61 to receive a projection or post 63 extending from the tension member 88. In this manner, the post 63 can move the visual indicator 91 proximally and distally in the slot 92 as the tension member 88 moves along the threaded shaft 87. The visual indicator 91 can also include an arm or tab 65 (FIG. 8) extending orthogonally to the post 63 and configured to engage an extension portion 71 located below the slot 92. In this manner, as the visual indicator 91 moves proximally along the inclined extension portion 71 of the slot, the visual indicator can be lifted relative to the tension member 88 by the tab 65. Conversely, as the visual indicator 91 moves distally along the extension portion 71, the visual indicator can be lowered relative to the tension member. The indicator therefore moves along an inclined path parallel to the slot 92. Motion of the visual indicator 91 relative to the tension member 88 as the tension member and visual indicator move proximally and distally is illustrated by double-headed arrow 73 (FIGS. 2 and 3). In this manner, the visual indicator 91 can remain visible to a user along the length of the slot 92. In some embodiments, the slot 92 can be covered by a transparent cover to protect the visual indicator 91 and to prevent, for example, a user's finger, from interfering with motion of the visual indicator.

The rotatable member 86 can be accessible through an opening 51 defined on a side portion of the first shell 50 and/or an opening 53 defined in a side portion of the second shell 52, as shown in FIG. 5. This can allow the rotatable member to be operated by the thumb, finger(s), or a combination thereof, of one hand. In the illustrated embodiment, the rotatable member 86 can be located below and adjacent the lever member 62. Additionally, the rotatable member 86 and at least the grip portion 66 of the lever member 62 can be substantially co-located along the longitudinal axis 35 of the balloon catheter 16. More specifically, the rotatable member 86 can be located such that a mid-sectional axis 23 (FIG. 1) of the rotatable member passes through or near the center of the slot 68. This can facilitate one-handed operation of the lever member and/or the rotatable member regardless of the position of the lever member in the slot without requiring the user to reposition their hand during use.

Figure 10:
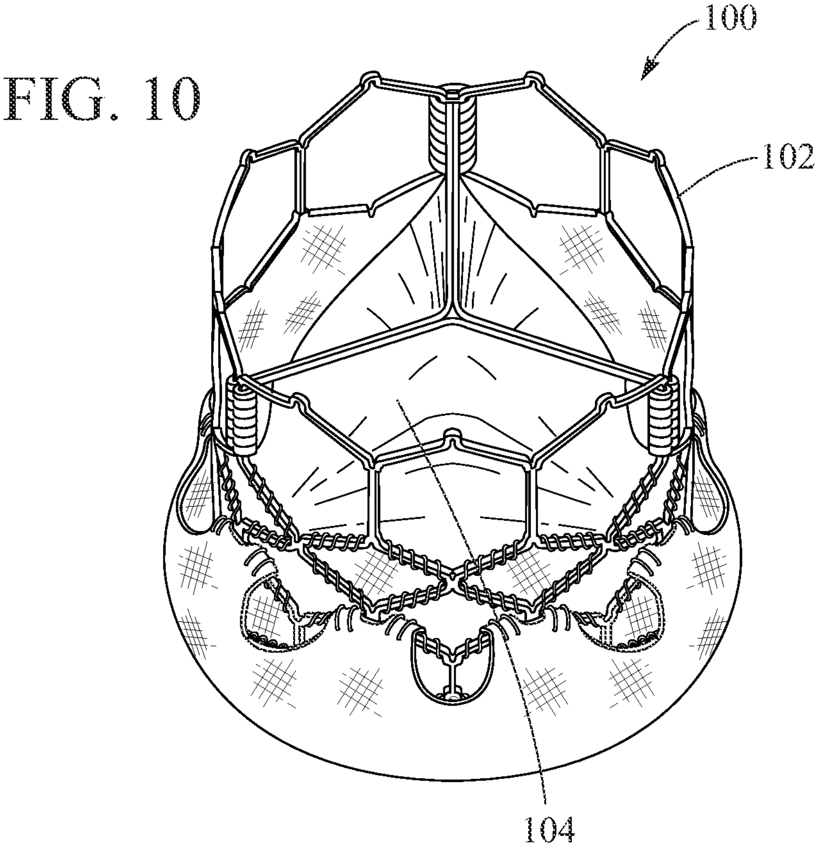
FIG. 10 is a perspective view of a prosthetic heart valve, according to one embodiment.
Figure 11:
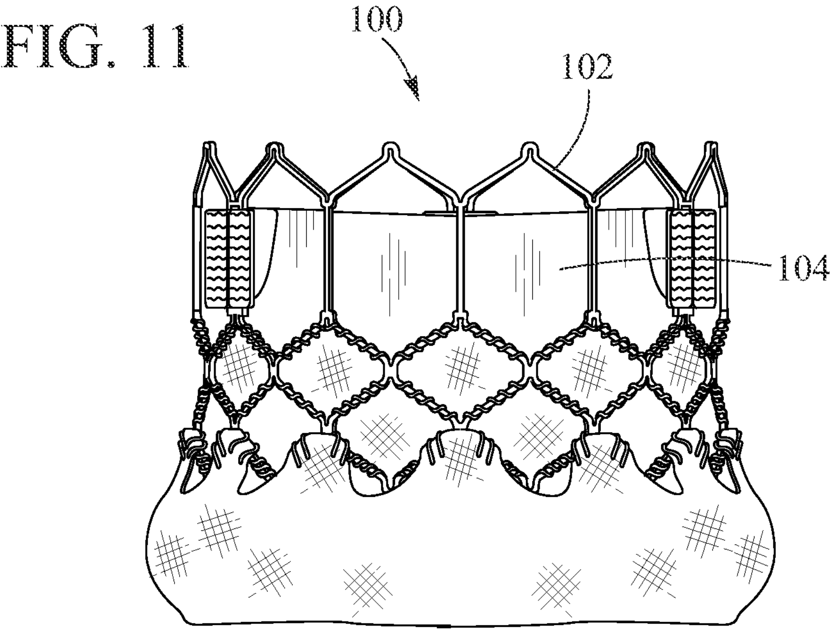
FIG. 11 is a side elevation view of the prosthetic heart valve of FIG. 10.

FIGS. 10 and 11 show a prosthetic heart valve 100, according to one embodiment, that can be used with the delivery apparatus 10. The prosthetic heart valve 100 comprises a frame, or stent, 102 and a leaflet structure 104 supported by the frame. In particular embodiments, the heart valve 100 is adapted to be implanted in the native aortic valve and can be implanted in the body using, for example, the delivery apparatus 10 described above. The prosthetic valve 100 can also be implanted within the body using any of the other delivery apparatuses described herein. Thus, the frame 102 typically comprises a plastically expandable material, such as stainless steel, a nickel based alloy (e.g., a nickel-cobalt-chromium alloy), polymers, or combinations thereof. In other embodiments, the prosthetic valve 100 can be a self-expandable prosthetic valve with a frame made from a self-expanding material, such as Nitinol. When the prosthetic valve is a self-expanding valve, the balloon of the delivery apparatus can be replaced with a sheath or similar restraining device that retains the prosthetic valve in a radially compressed state for delivery through the body. When the prosthetic valve is at the implantation location, the prosthetic valve can be released from the sheath, and therefore allowed to expand to its functional size. It should be noted that any of the delivery apparatuses disclosed herein can be adapted for use with a self-expanding valve.

Figure 12:
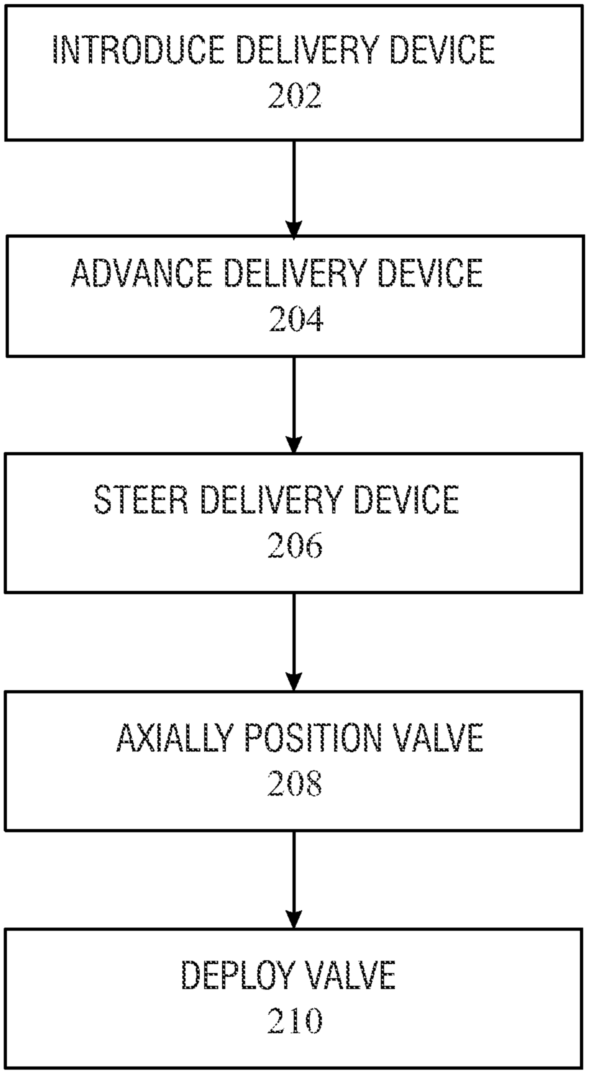
FIG. 12 is a flow chart illustrating a representative method of using a delivery apparatus.

With reference to FIG. 12, a representative method of implanting a prosthetic heart valve using the delivery devices disclosed herein can proceed in the following manner. At block 202, a delivery device can be introduced into the body of a patient via, for example, an incision in the femoral artery. The delivery device can comprise a handle portion and an elongated shaft extending from the handle portion. The shaft can have a distal end portion mounting a prosthetic heart valve in a radially compressed state.

At block 204, the distal end portion of the delivery device can be advanced toward the native heart valve until the prosthetic valve is within or adjacent the aortic arch, wherein the act of advancing comprises pushing the handle portion distally so as to push the delivery device distally through the patient toward the native heart valve.

At block 206, the device can be steered through the aortic arch by rotating a rotatable member coupled to the handle portion, wherein rotation of the rotatable member causes corresponding flexing or unflexing of the elongated shaft.

At block 208, the prosthetic heart valve can be axially positioned at a desired implantation position by moving a lever member coupled to the handle portion. Proximal and distal motion of the lever member can cause corresponding proximal and distal motion of the elongated shaft relative to the handle portion. In some embodiments, the prosthetic heart valve can be angularly positioned at a desired implantation angle by rotating the rotatable member coupled to the handle portion (e.g., at or near the aortic root) before, concurrently with, or after the prosthetic heart valve is axially positioned.

At block 210, after the prosthetic heart valve has been moved to the desired implantation position, the prosthetic heart valve can be deployed (e.g., radially expanded) to engage the annulus of the native heart valve.

Although the disclosed embodiments pertain generally to delivery devices and methods for implantation of prosthetic heart valves in the native aortic valve, it should be understood that the disclosed embodiments can be used to implant prosthetic devices at any location of the heart or elsewhere in the body. Additionally, although the disclosed embodiments pertain generally to transfemoral delivery of prosthetic devices, it should be understood that the disclosed embodiments can be adapted for use with, for example, transapical procedures, transaortic procedures, trans-subclavian procedures, transradial procedures, or trans-septal procedures. For example, the embodiments disclosed herein can be adapted for use with delivery devices for implanting self-expandable prosthetic valves, in which the axial position control assembly 60 and the angular position control assembly 84 can be coupled to an elongated guide catheter or shaft since a balloon catheter is not required.

Figure 13:
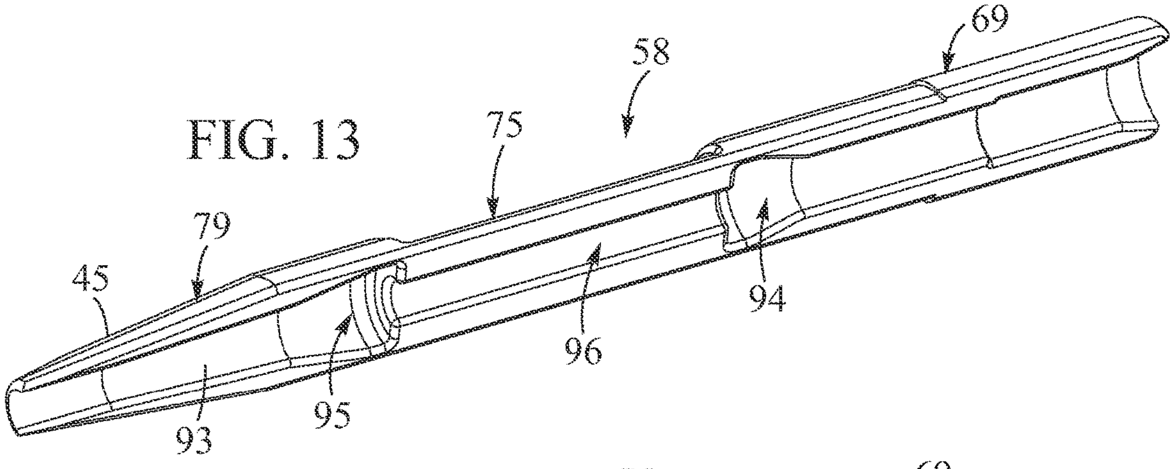
FIGS. 13-15 illustrate a representative embodiment of a protective cover.
Figure 14:
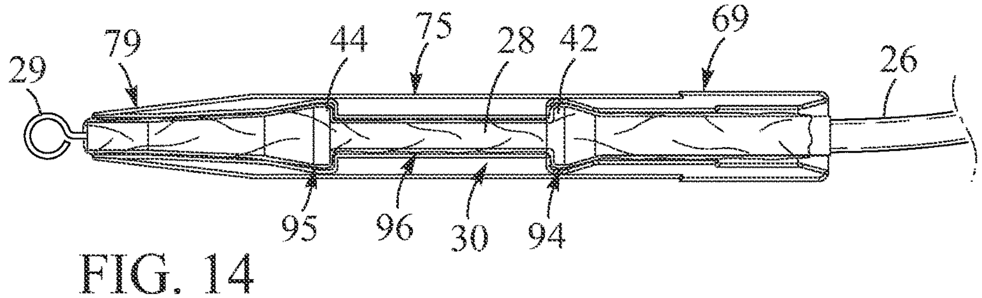
Figure 15:
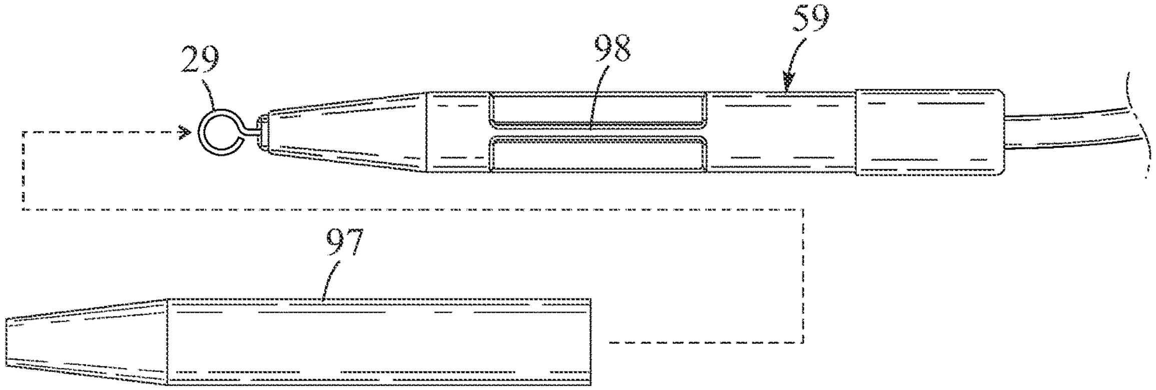

FIGS. 13-15 illustrate a representative embodiment of the protective cover 58 in greater detail. In the illustrated embodiment, the protective cover 58 can have a clam shell configuration and can comprise complementary first and second cover portions 45, 59 (see FIGS. 13 and 14) that encapsulate the balloon and, in certain configurations, a portion of the balloon catheter shaft 26.

FIG. 13 illustrates a representative embodiment of the first cover portion 45 including a proximal end portion 69, an intermediate portion 75, and a distal end portion 79. The first cover portion 45 can define a recess 93 extending from the proximal end portion 69, through the intermediate portion 75 to the distal end portion 79, and being shaped to substantially match the shape of the balloon 28 when it is folded around the proximal and distal collars 42, 44 (see FIG. 4). For example, the recess 93 can define a proximal collar-receiving portion 94 to receive the proximal collar 42, a distal collar-receiving portion 95 to receive the distal collar 44, and a central portion 96 to receive the inner shaft 34. FIG. 14 illustrates the balloon mounting portion 30 of the delivery device situated in the recess 93 such that the proximal and distal collars 42, 44 are received in the respective collar-receiving portions 94, 95, and the inner shaft 34 is received in the central portion 96.

The second cover portion 59 can define a complementary recess such that when the first and second cover portions are assembled together, the cover 58 defines a cavity shaped to accommodate the folded balloon 28 and the catheter assembly. The assembled cover portions 45, 59 can then be inserted inside a sheath or sleeve 97, which can keep the cover portions from separating, as illustrated in FIG. 15. In the illustrated embodiment, the first and second cover portions can also include rib members 98 extending along, for example, the intermediate portion 75, to provide strength and rigidity to the cover.

When situated inside the cover 58, the balloon 28 can be prevented from expanding substantially or otherwise deviating from its folded shape. Thus, after the balloon 28 is folded around the proximal and distal collars 42, 44, the balloon mounting portion 30 can be placed in the first and second cover portions 45, 59, and the sleeve 97 can be placed over the cover portions to form the assembled cover 58. The cover 58 can thereby protect the balloon from scratches, tears, etc., during assembly and shipping of the delivery device. Additionally, because the balloon 28 cannot substantially deviate from its folded shape when received in the cover 58, the cover can also facilitate pressure and/or vacuum testing of the balloon after assembly and/or in the operating theater. More specifically, the balloon 28 can be tested in the cover 58 by introduction of gas, fluid, or vacuum at the assembly location, and/or in the operating room prior to crimping of the valve 12, because the balloon is held in its folded configuration by the contoured cavity of the cover. Therefore, the physician does not need to perform any folding steps after balloon testing and prior to crimping the valve 12 on the balloon.

Figure 16:
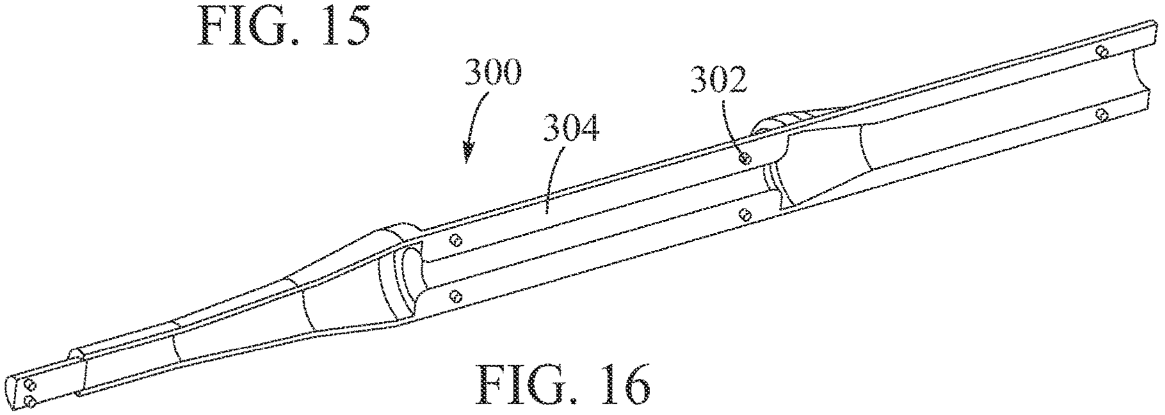
FIG. 16 is a perspective view of an alternative embodiment of a protective cover.

FIG. 16 illustrates an alternative embodiment of a first cover portion 300 including a plurality of projections 302 located along a mating surface 304 of the cover portion. In certain configurations, a complementary second cover portion can define corresponding openings to receive the projections 302 to aid in retaining the first and second cover portions in an assembled state.

Figure 17:
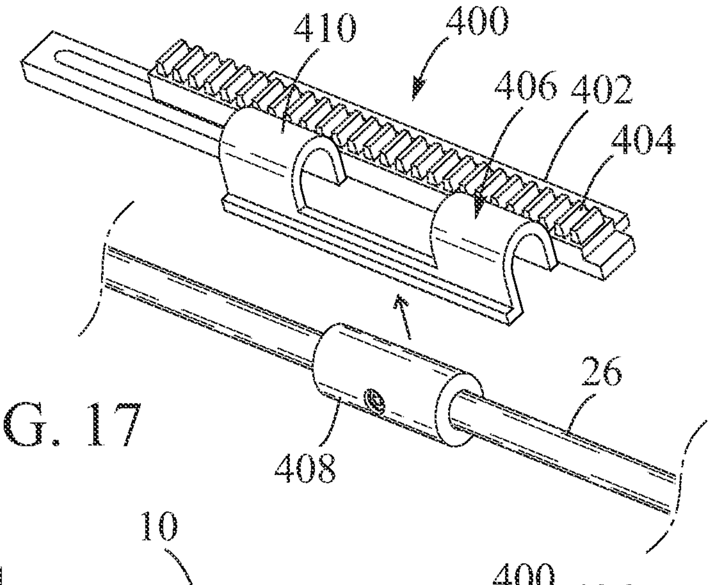
FIG. 17 is a perspective view of another embodiment of a rack member that can be coupled to a balloon catheter.
Figure 18:
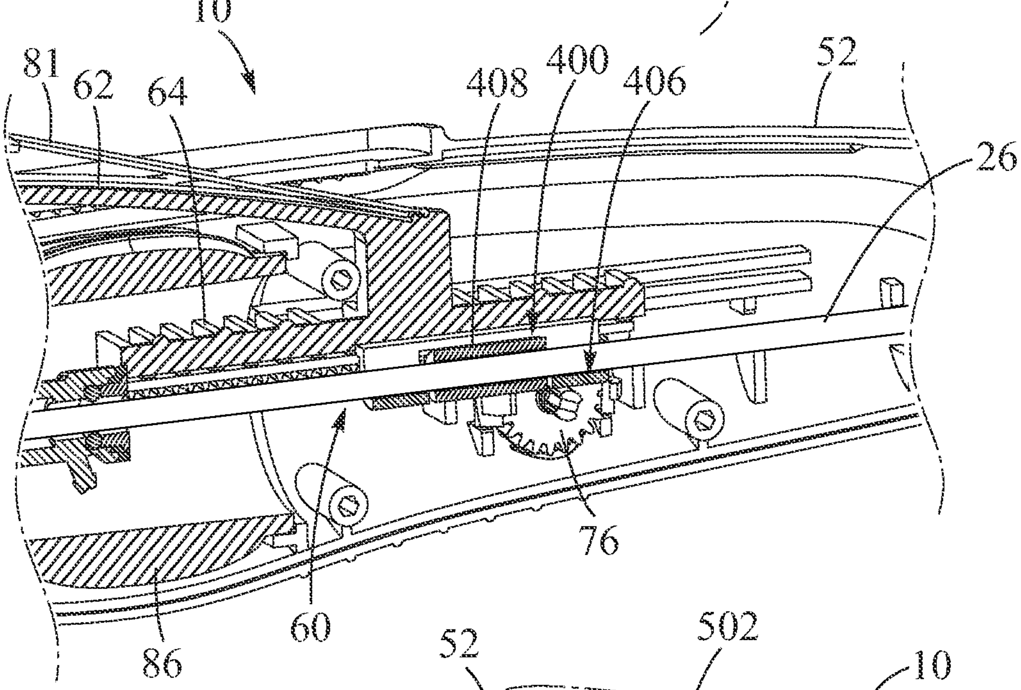
FIG. 18 is a cross-sectional view of a portion of the handle of the delivery apparatus illustrating the rack member and the balloon catheter coupled to the axial position control assembly.

FIGS. 17 and 18 illustrate another embodiment of a rack member 400 similar to the rack member 57 of the embodiment of FIG. 1. The rack member 400 can include a main body portion 402 including gear teeth or cogs 404 extending along at least a portion of the length of the main body. The rack member 400 can also include a cradle 406 positioned on a side of the main body 402 and configured to receive the balloon catheter shaft 26. For example, in the illustrated embodiment, a collar member 408 can be disposed about the balloon catheter shaft 26. The cradle 406 can be adapted to engage the collar member 408 (e.g., by snap-fitting) such that the collar member is received in the cradle. Curved arm portions 410 at either end of the cradle 406 can limit axial movement of the collar member 408 and, hence, of the balloon catheter shaft 26, relative to the main body 402 of the rack member. This configuration allows the collar member 408 to be coupled to the balloon catheter shaft 26 (e.g., by adhesive bonding and/or fasteners) at a desired position along the length of the balloon catheter shaft before final assembly of the delivery device. The balloon catheter-collar member assembly can then be easily coupled to the rack member 400. FIG. 18 is a cross-sectional view of the rack member 400 and the collar member 408 coupled to the balloon catheter shaft 26 and engaged with the axial position control assembly 60 within the second shell portion 52.

Figure 19:
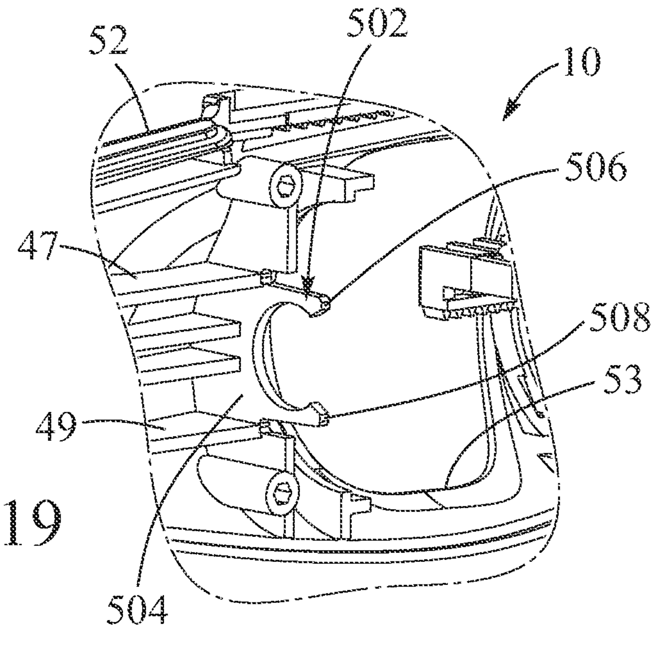
FIG. 19 is a perspective view of a portion of another embodiment of a shell of a delivery apparatus illustrating a coupling feature.

FIG. 19 is a cross-sectional view of a portion of another embodiment of the second shell portion 52 illustrating a coupling mechanism 502. The coupling mechanism 502 is located at the proximal end of the guide members 47, 49, and can include a base portion 504 and arms 506, 508 extending from the base portion. The coupling mechanism 502 can be configured to receive the threaded shaft 87 such that the arms 506, 508 engage the threaded shaft and prevent longitudinal movement of the threaded shaft during assembly and use of the device. For example, with reference to FIG. 8, the arms 506, 508 can be configured to engage the threaded shaft 87 at a recess 510 defined between first and second collar portions 512, 514 of the threaded shaft 87. By locating the arms 506, 508 between the collar portions 512, 514, the arms can prevent undesirable longitudinal movement of the threaded shaft 87, while allowing the threaded shaft to rotate to flex and unflex the guide catheter 14.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

The invention claimed is:

1. A delivery apparatus for implanting a radially compressible and expandable prosthetic heart valve in a native heart valve of the heart, the apparatus comprising:

a handle portion;

a balloon catheter assembly comprising an elongated balloon catheter shaft extending from the handle portion, the balloon catheter shaft including a proximal end portion coupled to the handle portion and a distal end portion, the balloon catheter assembly further comprising a balloon coupled to the distal end portion and configured to mount a prosthetic heart valve in a radially compressed state; and a two-piece protective cover that encapsulates the balloon, the cover comprising separable first and second cover portions defining a cavity shaped to accommodate the balloon; and wherein the cavity comprises a proximal portion, a distal portion shaped to receive a distal portion of the balloon, and a central portion shaped to receive a central portion of the balloon, wherein the proximal and distal portions of the cavity are larger in diameter than the central portion, and wherein the first cover portion comprises a plurality of projections configured to be received in openings of the second cover portion, the plurality of projections being shaped to prevent longitudinal movement of the first cover portion relative to the second cover portion when the first and second cover portions are assembled around the balloon.

2. The delivery apparatus of claim 1, wherein the first and second cover portions form a clam shell configuration.

3. The delivery apparatus of claim 1, further comprising a sleeve shaped to fit over the first and second cover portions.

4. The delivery apparatus of claim 1, wherein the proximal portion of the recess is shaped to receive a proximal collar located inside the proximal portion of the balloon and the distal portion of the recess is shaped to receive a distal collar located inside the distal portion of the balloon.

5. The delivery apparatus of claim 1, wherein the cover further comprises rib members.

6. The delivery apparatus of claim 5, wherein the rib members extend along the central portion of the cover.

7. The delivery apparatus of claim 5, wherein the cover defines recessed portions between rib members.

8. A method of testing the delivery apparatus of claim 1, the method comprising introducing a fluid into the balloon while the balloon is inside the cover.

9. A delivery apparatus for implanting a radially compressible and expandable prosthetic heart valve in a native heart valve of the heart, the apparatus comprising:

a handle portion;

a balloon catheter assembly comprising elongated inner and outer balloon catheter shafts extending from the handle portion, the outer balloon catheter shaft including a proximal end portion coupled to the handle portion and a distal end portion, the inner balloon catheter shaft including a proximal end portion coupled to the handle portion and a distal end portion, the balloon catheter assembly further comprising a distal collar mounted to the inner balloon catheter shaft, and a balloon folded around the distal collar and configured to mount a prosthetic heart valve in a radially compressed state; and a two-piece protective cover that encapsulates the balloon, the cover comprising separable first and second cover portions shaped to fit around the balloon, the cover defining a cavity shaped to accommodate the folded balloon and the distal collar, wherein the cavity comprises a distal portion shaped to receive a distal portion of the balloon and a central portion shaped to receive a central portion of the balloon, wherein the distal portion of the cavity is larger in diameter than the central portion, and wherein the first cover portion comprises a plurality of projections configured to be received in openings of the second cover portion, the plurality of projections being shaped to prevent longitudinal movement of the first cover portion relative to the second cover portion when the first and second cover portions are assembled around the balloon.

10. The delivery apparatus of claim 9, wherein the first and second cover portions form a clam shell configuration.

11. The delivery apparatus of claim 9, further comprising a sleeve shaped to fit over the first and second cover portions.

12. The delivery apparatus of claim 9, wherein the first and second cover portions define the cavity.

13. The delivery apparatus of claim 9, wherein the recess further comprises a proximal portion shaped to receive a proximal collar mounted to the outer balloon catheter shaft.

14. The delivery apparatus of claim 13, wherein the cover further comprises rib members.

15. The delivery apparatus of claim 14, wherein the rib members extend along the central portion of the cover.

16. The delivery apparatus of claim 14, wherein the cover defines recessed portions between rib members.

17. The delivery apparatus of claim 9, wherein a diameter of the distal collar is greater than a diameter of the outer balloon catheter shaft.

18. A delivery apparatus for implanting a radially compressible and expandable prosthetic heart valve in a native heart valve of the heart, the apparatus comprising:

a handle portion;

a balloon catheter assembly comprising an elongated balloon catheter shaft extending from the handle portion, the balloon catheter shaft including a proximal end portion coupled to the handle portion and a distal end portion, the balloon catheter assembly further comprising a balloon coupled to the distal end portion and configured to mount a prosthetic heart valve in a radially compressed state; and a two-piece protective cover that encapsulates the balloon, the cover comprising separable first and second cover portions defining a cavity shaped to accommodate the balloon; and wherein the cavity comprises a distal portion shaped to receive a distal portion of the balloon and a central portion shaped to receive a central portion of the balloon, and wherein the distal portion of the cavity is larger in diameter than the central portion, and wherein the first cover portion comprises a plurality of projections configured to be received in openings of the second cover portion, the plurality of projections being shaped to prevent longitudinal movement of the first cover portion relative to the second cover portion when the first and second cover portions are assembled around the balloon.

* * * * *